(12) United States Patent
Witte

(10) Patent No.: US 9,169,882 B2
(45) Date of Patent: Oct. 27, 2015

(54) TORQUE LIMITER

(75) Inventor: Peter Witte, Kiel (DE)

(73) Assignee: Stryker Trauma GmbH (DE)

( * ) Notice: Subject to any disclaimer, the term of this patent is extended or adjusted under 35 U.S.C. 154(b) by 1996 days.

(21) Appl. No.: 12/225,303

(22) PCT Filed: Mar. 14, 2007

(86) PCT No.: PCT/DE2007/000471
§ 371 (c)(1),
(2), (4) Date: Jun. 11, 2010

(87) PCT Pub. No.: WO2007/104296
PCT Pub. Date: Sep. 20, 2007

(65) Prior Publication Data
US 2011/0042176 A1 Feb. 24, 2011

(30) Foreign Application Priority Data
Mar. 15, 2006 (DE) ............... 20 2006 004 027 U

(51) Int. Cl.
| F16D 7/02 | (2006.01) |
| --- | --- |
| F16D 43/208 | (2006.01) |
| B25B 23/142 | (2006.01) |
| B25B 23/14 | (2006.01) |
| F16D 7/10 | (2006.01) |
| A61B 17/88 | (2006.01) |
| A61B 19/00 | (2006.01) |

(52) U.S. Cl.
CPC ............ *F16D 43/208* (2013.01); *B25B 23/141* (2013.01); *B25B 23/1427* (2013.01); *F16D 7/10* (2013.01); *A61B 17/8875* (2013.01); *A61B 2019/301* (2013.01)

(58) Field of Classification Search
CPC .... B25B 23/1427; B25B 23/141; B25B 23/14
USPC .......... 81/467, 472, 474, 473, 476; 192/41 A; 464/35, 37, 30
See application file for complete search history.

(56) References Cited

U.S. PATENT DOCUMENTS

| 2,668,426 A | 2/1954 | Hoover |
| 2,960,852 A | 11/1960 | Schroter et al. |

(Continued)

FOREIGN PATENT DOCUMENTS

| DE | 197 22 798 A1 | 12/1998 |
| DE | 199 03 863 A1 | 8/2000 |
| GB | 894 306 A | 4/1962 |

(Continued)

*Primary Examiner* — Hadi Shakeri
*Assistant Examiner* — Danny Hong
(74) *Attorney, Agent, or Firm* — Lerner, David, Littenberg, Krumholz & Mentlik, LLP

(57) ABSTRACT

A torque limiter has an outer sleeve whose interior wall possesses at least one peripheral groove and a plurality of recesses running parallel to the axis. An elastic ring is inserted in each groove. A rolling-element cage has the same number of slots as the number of recesses possessed by the outer sleeve that receives it. A plurality of the rolling elements that are inserted into the rolling element slots. The inner sleeve which slots into the rolling-element cage and whose exterior wall possesses the same number of V-shaped notches—running parallel to the axis—as the number of rolling element slots is provided. A tool or system is provided to restrict the relative torsion between the rolling-element cage and the outer sleeve between a first received position—and a second received position—when the outer sleeve is loosened by rotation and the rolling elements which slot into the notches on the inner sleeve change position vis-à-vis the recesses on the outer sleeve.

13 Claims, 4 Drawing Sheets

(56) References Cited

U.S. PATENT DOCUMENTS 3,067,597 A 12/1962 Sauerbrey
2009/0049961 A1* 2/2009 Chen .............................. 81/429

FOREIGN PATENT DOCUMENTS

JP  2005207475 A  8/2005
JP  2005344822 A  12/2005

* cited by examiner

TORQUE LIMITER

BACKGROUND OF THE INVENTION

The invention concerns a torque limiter, in particular a torque limiter suitable for the limitation of the torque of a surgical screwdriver.

Such a torque limiter for a surgical screwdriver is known from DE 600 04 376 T2 and U.S. Pat. No. 6,132,435. The mechanics of the torque limiter is highly sophisticated.

SUMMARY OF THE INVENTION

The invention is based on the task of creating a torque limiter which uses a simple mechanism.

The invention accomplished this task through an outer sleeve whose interior wall possesses at least one peripheral groove and a plurality of recesses running parallel to the axis, (one) elastic ring(s) inserted in the groove(s), one rolling-element cage with the same number of slots as the number of recesses possessed by the outer sleeve that receives it, a plurality of the rolling elements that are inserted into the rolling-element slots, the inner sleeve which slots into the rolling-element cage and whose external wall possesses the same number of V-shaped notches—running parallel to the axis—as the number of rolling-element slots, and the tool to restrict the relative torsion between the rolling-element cage and the outer sleeve between a first received position—when the outer sleeve is turned in the rotational direction whereupon the tool effects a transfer of the torque and the rolling elements align with the recesses and enter the inner sleeve from the notches under pressure from the elastic ring(s) having attained the maximum torque of transfer—and a second received position—when the outer sleeve is loosened by rotation and the rolling elements which slot into the notches on the inner sleeve change position vis-à-vis the recesses on the outer sleeve.

An alternative design consists of an inner sleeve whose exterior wall possesses at least one peripheral groove and a plurality of recesses running parallel to the axis, (one) elastic ring(s) inserted in the groove(s), a rolling-element cage adjacent to the interior sleeve with the same number of slots as the number of recesses, a plurality of the rolling elements inserted in the slots of the rolling-element cage, a rolling-element cage, adjacent to the inner sleeve, whose interior wall possesses the same number of V-shaped notches as the number of rolling-element slots, and the tool to restrict relative torsion between the rolling-element cage and the interior sleeve between a first received position—when the exterior sleeve is turned in the rotational direction whereupon the rolling elements lying in the notches of the external sleeve align with the recesses that they enter from the notches under the force of the elastic ring(s) having attained the maximum transferable torque—and a second received position—when the outer sleeve is loosened by rotation and the rolling elements that slot into the notches change position vis-à-vis the recesses.

The tool operates through the movement of the rolling-element cage vis-à-vis the rolling-element slots so as to create penetrative noses that enter the recesses running parallel to the axis.

The rolling elements may consist of pins or cylinders. The rolling element possessed by the cage may be in the form of needles.

The elastic ring(s) should preferably consist of (an) O-ring(s) manufactured from an elastic material.

The invention will be explained below by reference to drawings which will show

DETAILED DESCRIPTION

Figure 1:
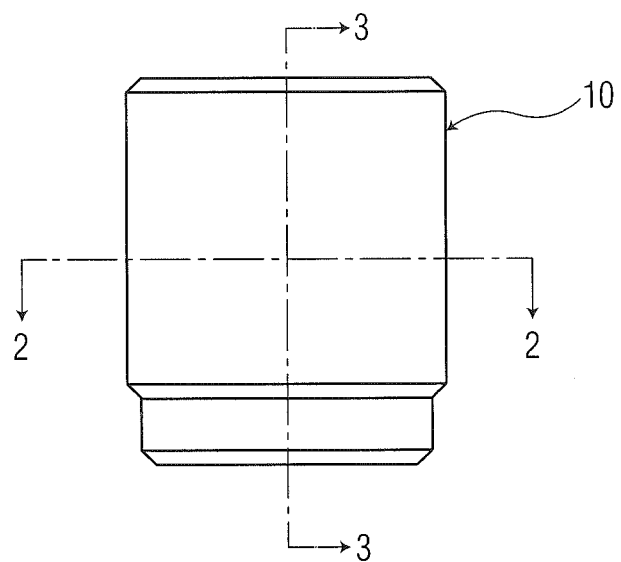
FIG. 1 is a view of the torque limiter.
Figure 2:
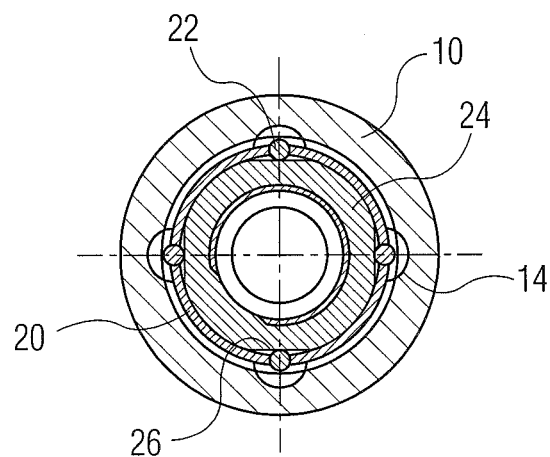
FIG. 2 is a cross-section along line A-A of FIG. 1.

The torque limiter consists of an outer sleeve 10 through which rotational force is exerted on the torque limiter. The inner wall of the outer sleeve 10 possesses at least one peripheral groove 12 and a plurality of recesses 14 that run parallel to the axis and therefore at right angles to the groove. An elastic O-ring 16 is inserted into each of the grooves 12.

The outer sleeve incorporates a rolling-element cage with the same number of recesses 14 as the number of rolling-element slots 18. A rolling element 22 capable of radial movement is slotted into each of the rolling-element slots 18.

The rolling-element cage 20 possesses a number of noses 28 that run parallel to the axis and penetrate the recesses 14 in the outer sleeve 10 that also run parallel to the axis; these noses 28 are narrower than the width of the recesses 14 so that the rolling-element cage 20 may be rotated at an angle to the outer sleeve until the sides of the noses 28 nudge against either side of the recesses 14.

The rolling-element cage 20 possesses an inner sleeve 24 in which the shaft of a screwdriver (not shown) is inserted. The external walls of the inner sleeve 24 possess V-shaped notches 26 which may be entered by the rolling elements 22.

In the first received position—upon turning the outer sleeve 10 in the torsional direction—the rolling elements 22 align with the recesses 14. The noses 28 that lie against one of the walls of the recesses transfer the torque from the outer sleeve 10 to the rolling-element cage 20. Upon the attainment of the maximum transferable torque, the rolling elements 22 exit the V-shaped notches 26 in the inner sleeve and penetrate the elastic rings 16 in the recesses 14 of the outer sleeve 10. This position does not permit any transfer of force between the inner sleeve 24 and the outer sleeve 10 that accompanies the rolling-element cage 20; further torsion is therefore impossible.

In the second received position—upon turning the outer sleeve in order to loosen it—the rolling elements 22 received by the notches 26 in the inner sleeve 24 change position vis-à-vis the recesses of the outer sleeve 10. The rolling elements are returned into the notches 26 under the pressure of the O-rings 16. The noses 28, which now lie against the other wall of the recess, effect a transfer of the torque from the outer sleeve to the rolling-element cage and therefore between the outer sleeve and the inner sleeve.

The maximum torque is determined by selecting the O-ring with the desired shore hardness or according to the number of rolling elements that are inserted.

Figure 3:
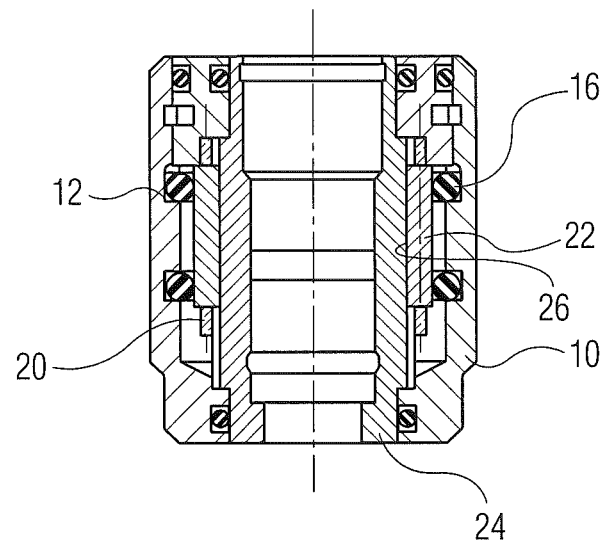
FIG. 3 is a cross-section along line B-B of FIG. 1.
Figure 4:
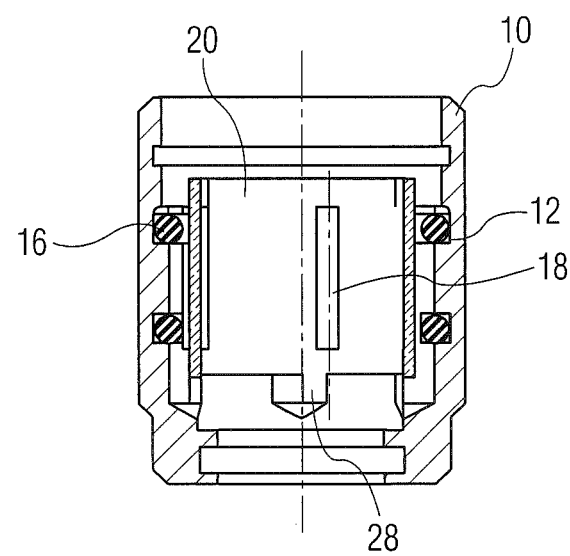
FIG. 4 is a cross-section along line B-B of FIG. 1—without the inner sleeve—in the rotational position.
Figure 5:
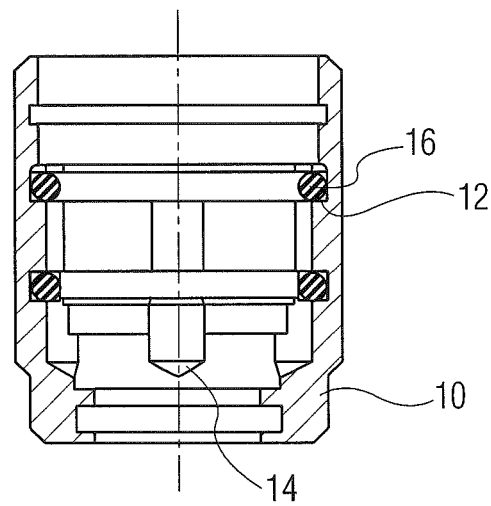
FIG. 5 is a cross-section along line B-B of FIG. 1 without the interior sleeve and the rolling-element cage.
Figure 6:
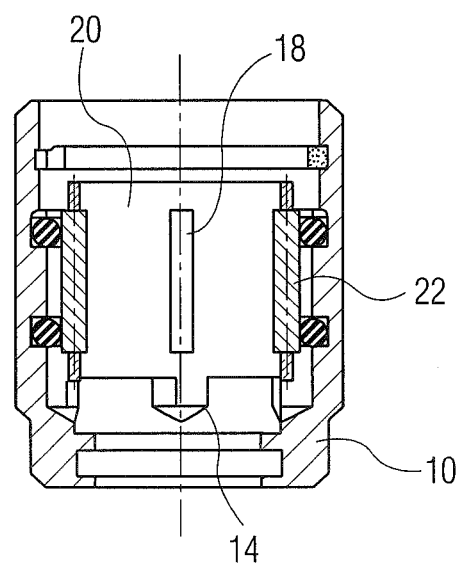
FIG. 6 is the same view as in FIG. 4 but showing the loosening position.
Figure 7:
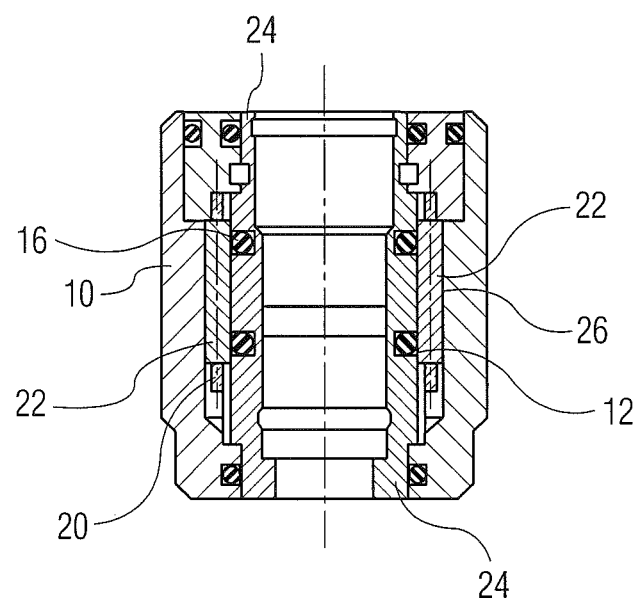
FIG. 7 is a cross-section of an alternate embodiment of the torque limiter where the circumferential grooves are formed on the inner sleeve and receive elastic rings.

In the alternative design which is shown in cross-section in FIG. 7 the grooves 12 and recesses 14 are formed on the inner sleeve 24 and the elastic rings 16 are inserted in the inner sleeve grooves 12 and the notches 26 are formed in the outer sleeve 10. FIG. 7 is similar to FIG. 3 except that the grooves 12 with elastic rings 16 are formed on the inner sleeve 24 and notches 26 are formed in the outer sleeve 10. The outer surface of inner sleeve 24 has a number of recesses 14 spaced around the sleeve running parallel to a longitudinal axis of the inner sleeve. The corresponding notches 26 extend axially along the inner wall of outer sleeve 10. Thus this embodiment is the inverse of the design of FIGS. 1-6.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A torque limiter comprising:
  an outer sleeve whose inner wall possesses at least one peripheral groove and a plurality of recesses each recess runs parallel to a longitudinal axis of the outer sleeve;
  an elastic ring inserted into each groove;
  a rolling-element cage received within the outer sleeve and which possesses a plurality of slots corresponding to the number of recesses;
  a number of rolling elements that are inserted into the rolling-element slots, each rolling element in contact with the elastic ring mounted in the outer sleeve,
  an inner sleeve received within the rolling-element cage and whose external wall possesses a number of V-shaped notches each running parallel to the longitudinal axis, the number the same as the number of rolling-element slots, and
  a tool which restricts the relative torsion between the rolling-element cage and the outer sleeve between a first received position when the outer sleeve is turned in the rotational direction whereupon the tool transfers the torque and the rolling elements align with the recesses and enter the inner sleeve from the notches under radial pressure from the elastic ring having attained the maximum torque of transfer—and a second received position—when the outer sleeve is loosened by rotation and the rolling elements which move into the notches on the inner sleeve changing position vis-à-vis the recesses on the outer sleeve.

2. A torque limiter, comprising:
  an inner sleeve, whose external wall exhibits at least one peripheral groove and a number of recesses spaced around an outer circumference of the inner sleeve each running parallel to a longitudinal axis of the inner sleeve;
  an elastic ring inserted into each groove,
  a rolling-element cage adjacent to the inner sleeve with a number of slots equal to the number of recesses,
  a plurality of the rolling elements that are inserted into the slots of the rolling-element cage, each rolling element in contact with the elastic ring,
  an outer sleeve adjacent to the rolling-element cage whose interior wall possesses the same number of V-shaped notches each running parallel to the axis as the number of rolling-element slots,
  a tool which restricts relative torsion between the rolling-element cage and the inner sleeve between a first received position —upon turning the outer sleeve in the torsional direction whereupon the rolling elements lying in the notches of the external sleeve align with the recesses that they enter from the notches under radial pressure from the elastic ring(s) having attained the maximum transferable torque—and a second received position—when the outer sleeve is loosened by rotation whereupon the rolling elements received by the notches change position vis-à-vis the recesses.

3. The torque limiter described by claim 1 or 2 wherein the method of restriction which consists of the movement of the rolling-element cage vis-à-vis the rolling-element slots which permits penetrative noses on the cage to enter the recesses in the outer sleeve that run parallel to the axis.

4. The torque limiter as claimed in claim 1 or 2 wherein rolling elements are in the form of needle rolling elements.

5. The torque limiter as claimed in claim 1 or 2 wherein the ring is an elastic ring consisting of an O-ring manufactured from elastic material.

6. A torque limiter comprising:
  an axially extending outer sleeve having an inner circumferential wall with at least one circumferential groove and a plurality of axially extending recesses spaced around the circumferential inner wall of the outer sleeve;
  a cage element received within the outer sleeve having a plurality of slots corresponding to the plurality of axially extending recesses on the outer sleeve inner wall rotatably mounted within the outer sleeve;
  a plurality of rolling elements with one rolling element mounted on each slot in the cage, the rolling elements capable of movement in the radial direction within each slot;
  an inner sleeve operatively connected to a screw driver, the inner sleeve mounted within the cage, the inner sleeve having an outer wall with a plurality of v-shaped axially extending notches for receiving one of the rolling elements; and
  an elastomeric ring mounted in the circumferential groove on the outer sleeve for contacting and radially biasing each of the rolling elements towards the v-shaped notch in the inner sleeve outer wall.

7. The torque limiter as set forth in claim 6 wherein the cage element includes a nose element for engaging opposite sidewalls of the axial recess in the outer sleeve inner wall.

8. The torque limiter as claimed in claim 6 wherein rolling elements are in the form of needle rolling elements.

9. The torque limiter as claimed in claim 6 wherein the ring is an elastic ring consisting of an O-ring manufactured from elastic material.

10. A torque limiter comprising:
  an outer sleeve having an inner wall possessing at least one circumferential groove and a plurality of recesses spaced around an inner circumference of the outer sleeve inner wall that each run parallel to a longitudinal axis of the torque limiter;
  an elastic ring inserted into each groove;
  a rolling-element cage received within the outer sleeve and which possesses a plurality of longitudinally extending rolling element slots corresponding to the number of recesses;
  a plurality of rolling elements that are inserted into the rolling-element slots, each rolling element in contact with the elastic ring,
  an inner sleeve received within the rolling-element cage having an external wall possessing a number of elongated V-shaped notches each running parallel to a longitudinal axis of the sleeve, the number of elongated v-shaped notches the same as the number of rolling-element slots, and a tool which restricts the relative torsion between the rolling-element cage and the outer sleeve between a first received position when the outer sleeve is turned in a first rotational direction whereupon the tool transfers the torque and the rolling elements align with the recesses and enter the inner sleeve from the notches under radial pressure from the elastic ring having attained the maximum torque of transfer—and a second received position—when the outer sleeve is loosened by rotation in a second direction and the rolling elements move radially into the notches on the inner sleeve by tangentially changing position vis-à-vis the recesses on the outer sleeve.

11. The torque limiter as claimed in claim 10 wherein rolling elements are in the form of needles.

12. The torque limiter as claimed in claim 10 wherein the ring is an elastic ring consisting of an O-ring manufactured from elastic material.

13. A torque limiter comprising:

a cylindrical outer sleeve extending along a central longitudinal axis having an inner surface comprising two circumferential grooves and a plurality of recesses each extending along the inner surface parallel to the longitudinal axis, the outer sleeve capable of receiving a rotational force;

an elastic ring mounted in each circumferential groove of the outer sleeve;

a cylindrical inner sleeve received within the outer sleeve extending along the central longitudinal axis, the inner sleeve having an outer cylindrical surface with a plurality of v-shaped notches each extending parallel to the longitudinal axis, the v-shaped notches aligned with the plurality of recesses on the inner surface of the outer sleeve;

a rolling element cage intermediate the outer and inner sleeve, the cage including a plurality of rolling elements for transferring the rotational force from the outer to the inner sleeve, each rolling element being in contact with the elastic rings and received within the v-shaped notches on the inner sleeve outer surface, the rolling element cage having nose elements extending into the recesses in the outer sleeve, the nose elements have a width narrower than a width of the recess so that under a maximum rotational force relative movement between the rolling element cage and the outer sleeve allows the rolling element to compress the elastic ring and tangentially move out of the v-shaped notches in the inner sleeve thereby preventing the transfer of rotational force from the outer to the inner sleeve.

\* \* \* \* \*